United States Patent [19]
Tavori

[11] Patent Number: 5,724,025
[45] Date of Patent: Mar. 3, 1998

[54] PORTABLE VITAL SIGNS MONITOR

[76] Inventor: Itzchak Tavori, P.O. Box 434, 46103 Herzlia B, Israel

[21] Appl. No.: 601,641

[22] Filed: Feb. 14, 1996

Related U.S. Application Data

[63] Continuation-in-part of Ser. No. 326,421, Oct. 20, 1994, abandoned.

[30] Foreign Application Priority Data

Oct. 21, 1993 [IT] Italy .......................................... 107351

[51] Int. Cl.$^6$ .......................................... G08B 23/00
[52] U.S. Cl. .......................... 340/573; 128/630; 128/639; 128/734
[58] Field of Search ................ 340/573; 128/734, 128/630, 639

[56] References Cited

U.S. PATENT DOCUMENTS

5,353,793 10/1994 Bornn .......................... 128/639
5,416,469 5/1995 Colling .......................... 340/573

*Primary Examiner*—Glen Swann
*Attorney, Agent, or Firm*—Mark M. Friedman

[57] ABSTRACT

A system for monitoring vital signs of a live body includes an inquiring device; and a portable monitoring device. The monitoring device includes an electrical circuit, which, in turn, includes a controller, data storage, and input ports. The electrical circuit is designed to read inputs and store data. The monitoring device further includes a number of sensors which are connected to the electrical circuit, each of the sensors detecting a property of the body. The device also includes an alarm mechanism which is designed to activate when a predetermined set point stored in the data storage is exceeded. The device further includes a mechanism for transferring stored data or received inputs to the inquiring device, further allowing the downloading of data and the setting or changing of one or more set-points of said alarm mechanism. Finally, the monitoring device includes a housing for holding the electrical circuit and sensors, as well as the communication means, the alarm device and the power supply.

18 Claims, 7 Drawing Sheets

PORTABLE VITAL SIGNS MONITOR

CROSS-REFERENCE TO RELATED APPLICATIONS

This is a Continuation-in-Part of U.S. Ser. No. 08/326,421, filed 20 Oct. 1994, now abandoned, which is based on Israel 107351, filed 21 Oct. 1993.

FIELD AND BACKGROUND OF THE INVENTION

The present invention relates to a device for monitoring, data collecting and alarm signaling relating to the condition of a live body. In particular, the present invention relates to the use of such a device as an on-line vital signs monitor for medical and personal needs.

Suspected health problems usually requires a doctor to monitor a patient on a daily or weekly basis. Today, in order to be monitored, the patient is required to come to a certain health facility, which demands the expenditure of time, bed space and the time of highly qualified personnel.

In typical hospitals, general patient information, including pulse, blood pressure and temperature, is collected for all patient twice a day. The information is used as basis for medical decisions. The time required to complete such a chore is enormous. For example, to gather the temperatures of the patients, thermometers have to be sterilized and then distributed to the patient population. The thermometers must then be collected and read and the patient's chart marked accordingly. The process is time consuming and is error prone during the data collection and processing phase because of the absence of certain patients from the ward, inaccurate readouts from mercury thermometers, and lack of attention of overworked personnel.

As a further example, pregnant woman are today required to monitor fetus pulse and labor progress during last third period of the pregnancy. Such monitoring requires rather frequent periodic visits to the doctor's office and further requires connection to a monitor for a period of 30 minutes or more, which is highly inconvenient and time-consuming. In addition, such visits are wasteful of medical resources, including but not limited to, the monitors themselves and the time of skilled personnel.

Numerous monitoring and/or measuring devices are commercially available. These include thermometers which save the last ten readings, portable ECG monitors, hand-held blood pressure measurement devices, and even a wrist watch which measures and stores pulse rate and blood pressure. All the above-mentioned devices are expensive and are dedicated to certain measurements which are electronically implemented during manufacturing stage. These devices either do not allow the managing physician to retrieve accumulated historical data by electronic means, or strictly limit his ability to do so. In addition, the devices do not allow the physician to focus on particular data of interest.

Thus, for example, a portable ECG device may be able to measure the pulse rate using a pre-determined sequence, while a sophisticated apparatus will also measure blood pressure. However, more information, such as temperature, breathing rate, skin pH and/or salinity, concentration of oxygen in the blood, and the like, is neither measured nor stored.

The collection and storage of such additional data requires additional measuring and data collection devices which are bulky and which consume time, effort and sometimes bed space and which may be beyond the financial means of the patient. In addition, the interpretation of such measurements requires the judgments and interpretation of qualified personnel, which is wasteful of the time of qualified personnel and of funds.

Moreover, present systems do not allow the combination of the readings of several sensors so as to form a more definitive diagnosis. Thus, for example, if only blood pressure is measured and is found to be abnormal, no definitive conclusions can be drawn. However, as a non-limiting example, if both blood pressure and temperature are measured simultaneously then one can make more definitive diagnoses based on the two measurements. For example a low blood pressure combined with a high temperature might present a different diagnosis than a low blood pressure combined with a low temperature.

Several patents disclose various monitoring devices. For example, IL 37218 discloses a portable cardiac monitor which is a dedicated device for measuring electrical impulses of the heart. There is no possibility of downloading appropriate software, or store and compare to fixed set-points. The same applies for IL 86010 which discloses an apparatus for measuring blood pressure.

IL 82888 discloses an automatic apparatus for measuring blood pressure which includes a pump, an inflatable sleeve and a bench-mounted measuring unit. The device is bulky and non-portable and has no data logging capability. The device cannot be downloaded with software for forced measurements and alarm set-points, and is dedicated to specific operations.

IL 68613 discloses a disposable detector which is dedicated to the taking of thermal measurements. The disclosed device includes a thermocouple, a cellular isolator and an adhesive layer.

IL 75274 discloses a body-hugging instrumentation vest designed to be worn over the entire torso, in which any sensor can be mounted. Such a device cannot perform data logging or alarm and is bulky and inconvenient for the user.

IL 63889 discloses an apparatus for automatically positioning body performance sensors.

IL 52973 discloses an identification bracelet on which data are to be attached by writing.

SUMMARY OF THE INVENTION

The present invention is of a portable multi-sensor vital signs monitor, which can read and store measured or raw data, which can be downloaded with related data such as personal identification parameters, operating software, forced measurement software, alarm set points, and which has the capability of conveniently transmitting its logged data to another data retrieving system. The device has the further capability of being conveniently mounted on a monitored body, for example, with a strip of adhesive bandage or with an adhesive layer which is implemented on it, wherein.

The device is capable of being mounted comfortably on the person or animal being monitored, has small dimensions and body hugging capability. The device can be mounted on a limb, on the torso, neck or belly, or on the back or any place on the monitored body. The device can be moved all over the body to accommodate various medical diagnostics procedures. Furthermore, measurements are taken continuously or intermittently as preset by the operating software. The data are either continuously or intermittently transmitted to a stationary data retrieving system or stored for further or later processing. Preferably, the device has the possibility to download software in order to change instructions and upper lower limit set points, which, when exceeded either instantaneously or integrally, an alarm is set off to indicate to the user or nearby personnel that professional medical attention is to be sought. The data can be transmitted to a pre-stored database of symptoms which allows the physician or other attending personnel to view and/or display current data status, history, symptoms, possible diagnostics and proposed remedy. Alternatively or additionally, the data can be used to build up a database of actual collected data for the individual patient and/or for the patient population as a whole. Such a database makes is possible to later carry out various analyses of the patient and/or of a large patient population. In certain applications it may be desirable to further indicate to the physician the result of proposed remedial actions and the anticipated behavior of the body during recovery. Eventually, the measured signals will show when and how the body reacts to medication and help monitor the healing process. As a non-limiting example, a patient have high blood pressure can be given medication with prescribed dosage and timing. In this case, the doctor is working in an open loop control mode and needs to rely entirely on the patient for the proper administration of the medication. There is no way for the doctor to determine whether the patient used the proper dosage and timing unless physiological measurements are taken, closing off the otherwise open control loop.

Furthermore, duplications of paperwork carried out during check-in is minimized. As first aid is administered, patient personnel records are input into the monitor and transferred to any inquiring data collecting system when patient is transferred between emergency medical care to ward and in between wards.

It is an object of the present invention to provide a device which is especially adapted for measuring vital signs of the human body while in contact with the body. It is to be noted that a device according to the present invention is not limited to applications relating to the human body but can be used also to monitor vital signs of any living creature, for example, live cattle.

According to a broad aspect of the invention there is provided a device for measuring vital signs, the device having an electrical circuit which includes a controller or processor, various sensors, a switching element for alternatively connecting and disconnecting sensors, an alarm device, a communication means, a housing and mounting means and a power supply.

The electrical circuit is connected to various sensors which changes its output according to the physics of its measurement.

The electrical circuit has data storage capability to store outputs coming from various sensors which changes its output.

The device further includes an alarm device which will activate when a pre determined set-point or set-points stored in the data storage capability is or are exceeded.

The device incudes communication means which allow data transfer of stored data or on-line measured data to an inquiring system, and which permit operator download measuring logics and sequence and the changing set-point or set-points of the alarm device. Data transfer may be by any suitable means, including but not limited to using optical impulses or electronic wireless transmission.

The device includes a substantial base with at least two electrodes which forms a means for mounting a plurality of sensors in contact with measured body.

Finally, the device includes a housing and mounting means which holds the electrical circuit with the sensors, the communication means, the alarm device and the power supply comfortably to the measured body, in order to perform the required tasks.

BRIEF DESCRIPTION OF THE DRAWINGS

The invention is herein described, by way of non-limiting example only, with particular regard to a device for measuring, monitoring and data collecting of vital signs, with a system and method for use therewith for medical diagnosis and for providing a warning or alarm indication to the patient in case of probable need of medical assistance or consultation, with reference to the accompanying drawings, wherein.

DETAILED DESCRIPTION OF PREFERRED EMBODIMENTS

Figure 1:
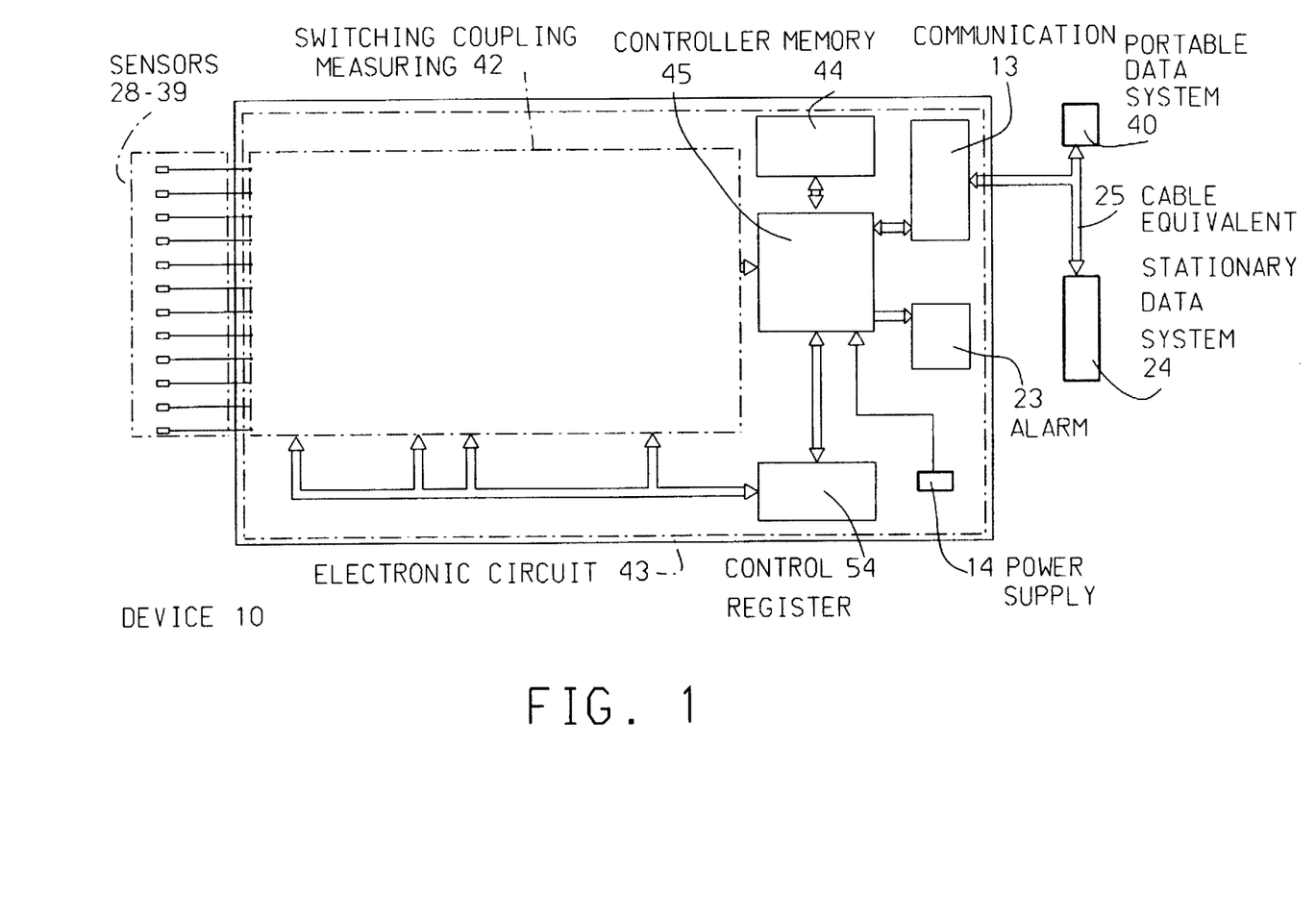
FIG. 1 shows schematically a block diagram illustrating the basic construction of the vital signs monitor of the present invention.

FIG. 1 is block diagram of a stand alone device according to the invention depicted generally as 10, comprising.

a switching-coupling- measuring measurement subsystem portion, 42, which is used to connect, disconnect, and measure sensor outputs;

a Controller device, 45, (that can be realized, for example, by using a CHIPS F8680, available from CHIPS, California, USA, which is capable of supporting directly a keyboard, LCD display, modem communication, memory, and other computer peripherals, has programmable pins logic, and configuration and status dam, or by using an Intel 80C196, which has its own A/D converter and multiplexer, can be used as a latch to activate sensors, supports RS-232 communication, memory, high-speed i/o, and has dual pulse-width-modulator (PWM) system, either of which functions as the controller of device, 10, which is provided with an operating instruction set by downloading the instruction set to device 10 and storing the instruction set in device 10, controller, 45, thereby functioning to operate device, 10;

Memory with data storage capability, 44, which can be realized as Flash memory, available from Intel corporation, as a dynamic random-access-memory (D-RAM) or static random-access-memory (S-RAM), available from leading manufacturers, or other memory systems known in the prior art, for recording events, and storing the instruction set;

Communication means, 13, for example, an RS-232 interface which is used to send and receive data and instruction sets; and, Alarm device, 23, which may be an annunciator, for providing audible warning to notify that an event had occurred. The RS-232 interface may be realized by any of many industry-standard integrated circuits which perform this function, such as the LT1133. Further, more than one portable vital signs monitor unit, 10, of the present invention, may be located on one patient, in which case the RS-232 interface may be used to provide communication between the monitor units, for example, in a "multi-drop" relationship, in which any of the units may communicate with inquiring device, 24 or 40.

An event is defined as a monitored combination of measured parameters exceeding a set-point limit, indicating possible need for medical attention or consultation.

Control register and decoder, 54, which can be realized as any standard TTL decoder such as a 74HC238, is used to send control signals to switching-coupling-measuring portion, 42, and to sensors attached to device 10. A power supply, 14, is provided.

The instruction set is, in effect a high-level language, such as is found in an electrical test set, such as is available from Teradyne, Boston, America. The instruction set programs the sequence of measurements to be made, which excitation source is to be used, if any, which measurement device is to be used, the connections which are to be made by a switch or relay connection matrix, test limits, including, here, combinations of test limits, based on which logical decisions will be made concerning whether to sound a warning alarm, and which severity of warning alarm indication is to be given. The instruction set provides, implicitly, the diagnostic software of the portable vital signs monitor, since the instruction set operates logically on the measurements "symptoms" to "diagnose", to determine whether a warning alarm indication is to be given, and what severity of warning alarm indication is to be given.

The components which are used to realize above mentioned functions, are connected by an electronic circuit, 43, which is used to distribute power from power supply, 14, and direct electrical pulses between the above-mentioned functions.

A "stationary", inquiring, data retrieving system, 24, which may be realized as general purpose computer, is connected via a cable-equivalent, 25, to communication means, 13, which provides bi-directional communication and transfer of data and instruction set from inquiring device 24 to memory 44, in device, 10, and to down load data and instruction set to be stored in memory 44.

"Stationary" inquiring system, 24, is provided for downloading the instruction set into the portable vital signs monitor device, 10, and for receiving measured data from device, 10, and for performing more detailed diagnoses than those usually provided in portable device, 10. A "portable" data retrieving system, 40, such as a palmtop computer, may alternatively be used to perform the tasks of "stationary" data retrieving inquiring system, 24.

Cable-equivalent 25 may be realized simply as wire cable, however other connecting techniques known in the prior art may be used, such as optical communication used to transfer data in between computer peripherals, line modem or cellular modem, electromagnetic wireless communication, such as radio, optical (e.g., IR, visible), and the like. The wireless communication may also include coupling to a Global Positioning System (GPS) to inform inquiring system 24 or 40 of the exact position of the patient. This is useful for locating a disabled patient.

Alarm device 23 can be realized as an audio alarm such as a speaker or piezo-electric buzzer, for example. Alarm device 23 may be used to generate various audible signals of different rates and/or pitches corresponding to the detected condition of the monitored body, visually, by miniature lamp arrays color coded, bargraph or alpha-numeric displays, such as are available from H.P., U.S.A., or L.C.D displays such as are available from Seiko, Japan.

Sensors 28–39 are used to transform physical phenomena into manageable values such as capacitance, inductance resistance, voltage, current, frequency, TTL level, and the like. This data is transferred to the switching-coupling-measuring element, 42, in which the data is transformed into digital data. Element 42, may be a readily-purchased item, such as a Keithley Model DAS-20 High-Performance Analog & Digital Interface Board, or similar, such as have been available in the industry for many years. These provide input multiplexing, amplification, sample-and-hold, analog-to-digital and digital-to-analog conversion, as well as including timing and data buffer and control functions as required for interfacing to personal-computer (PC)—type computers.

Controller 45 manages the digital data received and performs the instructions kept in memory 44 as the instruction set. Controller 45 manages the data and distributes it via electronic data-acquisition circuitry, 43, per the instruction set, to memory 44, to be recorded for later processing. The controller may send data to communication means, 13, for transmission to "stationary" data retrieving inquiring system, 24, or by "portable" data retrieving inquiring system 40. Controller, 45, may be used to convert measured data to other scales, such as resistance data of a RtD temperature sensor to temperature in °C. or in °F.

In case of a sensor signal other than previously defined in the instruction set, the controller may send a signal to alarm device 23 to notify that a signal exceeds the individual test limits or combination of test limits provided in the instructions loaded in the instruction set.

The controller also manages control register, 54, which co-ordinates the matrix connections to sensors 28–39 via the correct path in the switching-coupling-measuring element 42, per the loaded instruction set.

Figure 2:
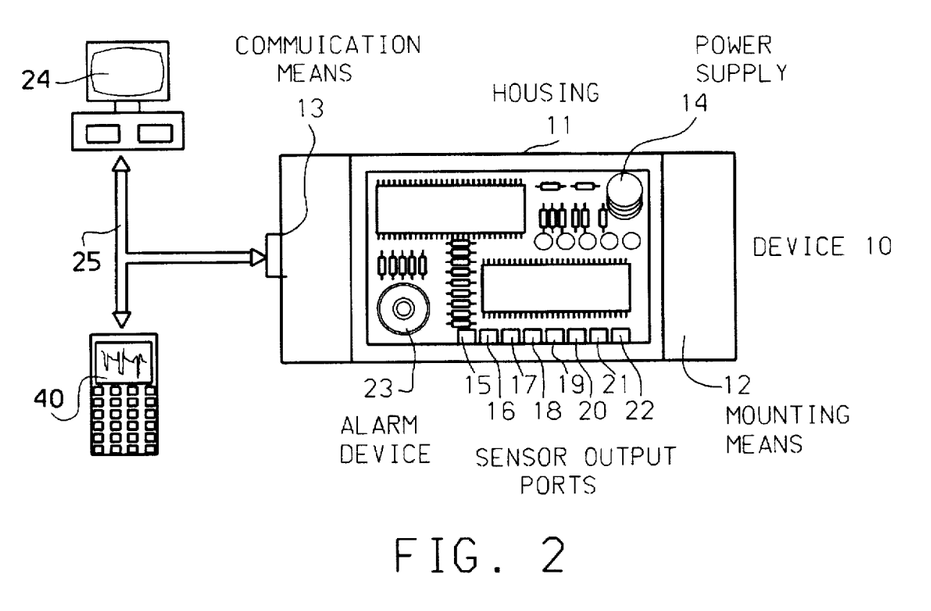
FIG. 2 shows schematically a device according to the present invention.

FIG. 2 shows a stand alone device according to the invention, depicted generally as 10, and comprising a housing, 11, having on a first side thereof, mounting means, 12, which overhangs housing, 11, an outwardly projected communication means, 13, a port for connection to power supply, 14, sensor output ports, 15–22, and alarm device, 23.

Housing, 11, contains an electrical circuit (not shown in FIG. 2) comprising controller means and data storage capability, which is connected to sensor output ports, 15–22, to alarm device, 23, to power supply, 14, and to communication means, 13.

Figure 3A:
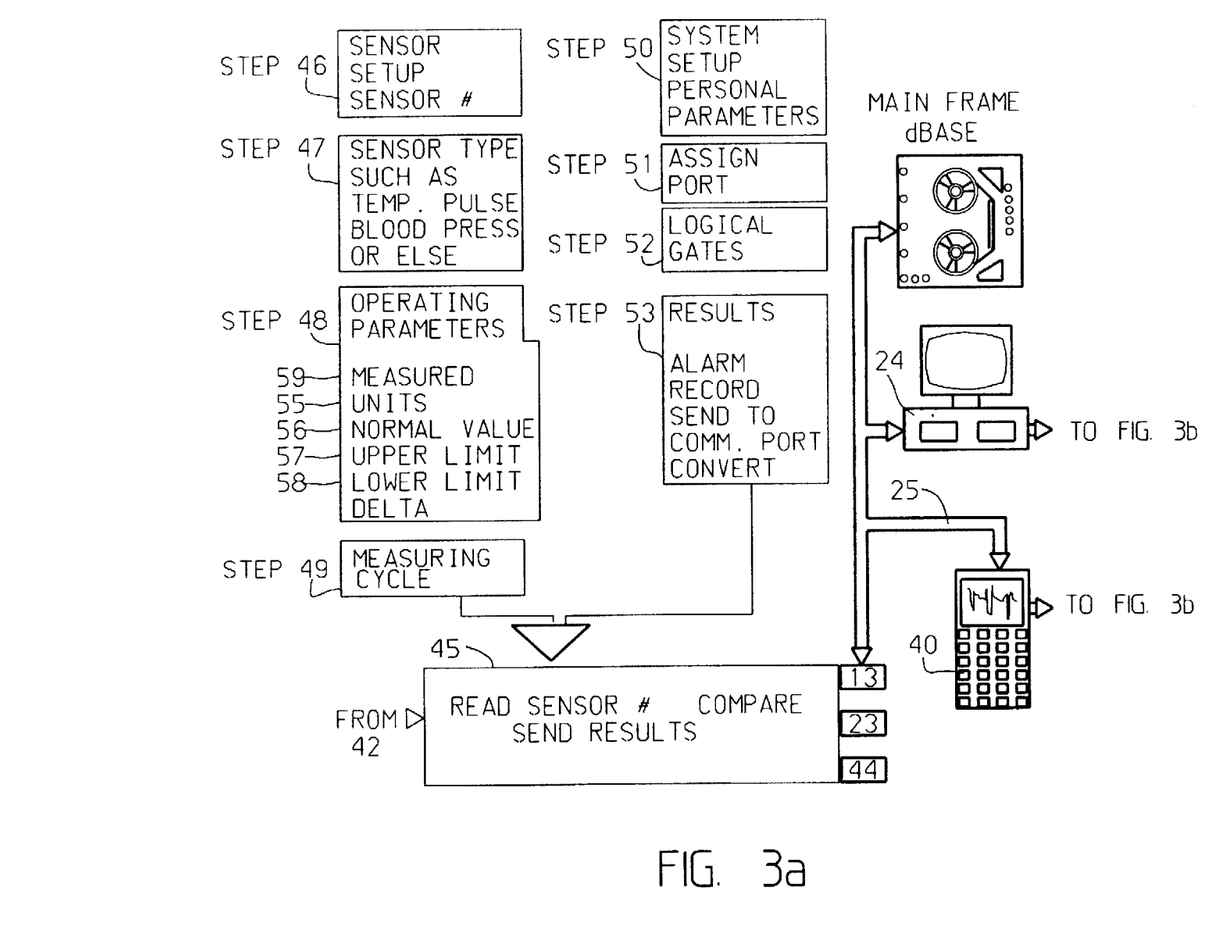
FIG. 3A shows schematically the device with an instruction set.

The managing physician may communicate with device, 10, and down-load instruction set, as shown in FIG. 3.

FIG. 3 shows one possible flow chart for defining the operation of an individual sensor, as may be specified in the instruction set.

Sensor setup, step 46, includes sensor operating information for one sensor and sensor number. For example, sensor 35 will now be defined. This procedure is relevant to any one of sensors 28–39. Sensor type, step 47, defines what is the information available from this sensor such as pulse, blood pressure, temperature, or else. Operating parameters, step 48, includes to what units, 59, this sensor is transforming physical phenomena, i.e., capacitance, inductance resistance, voltage, current, frequency, TTL level and similar, the expected normal values, 55, the upper limit of the signal, 56, the lower limit, 57, and at least one value, such as delta, 58, which has a value depending on normal value 55 and the upper/lower limits, 56 and 57, respectively. Delta can take the form of a simple value or may be a mathematical equation. Measuring cycle, step 49, may include instructions to measure sensor, 35, every predefined time interval such as every so many HH:MM:SS, or at a known hour such as 2:00 AM, or with some other measurement frequency, or according to some other appropriate time measurement pattern according to which sensor 35 ought to be measured.

The system setup, step 50, may include personal information of the patient and information where to connect the sensor and what to do with sensor 35 measured signal. Port assigning, step 51, includes information to what sensor ports, 15–22, shown in FIG. 2, sensor 35 is to be connected. Logical gates, step 52, includes logical IF, IF-THEN, AND, OR, NOR, NOT, and similar instructions allowing a combination of several sensor's output to be concluded into one conclusion. If we write logical operations as capital letters with periods on either side, then, for example, we might have, ".IF. sensor 35 signal .AND. sensor 36 signal is .GREATER THAN. (a specified limit value), .EQUALS. TRUE. .THEN. an event is defined to have occurred, and a warning alarm indication is given". The patient may then go to hospital or physician, or transfer data to the inquiring unit for more detailed diagnosis, according to the severity of the warning alarm indication given by the portable monitoring unit in response to the event.

Results in step 53 defines what to do with data, whether to send it to memory, 44, to be recorded for later processing, or to send it to communication means, 13, to be sent to stationary or portable data retrieving inquiring systems, 24 or 40, to send signal to alarm device 23.

Controller, 45, compares measured data of sensor 35 to normal upper and lower values, 55, 56, and 57, respectively. Signals which exceed upper or lower limit are sorted as to results 53 defined by a managing physician, in the patient's unique instruction set or in a "normal-patient" instruction set, i.e., recorded in memory, 44, sent to communication means, 13, to be retrieved by stationary or portable data retrieving inquiring systems, 24 or 40, or a signal is sent to alarm device, 23, to bring to the attention of the bearer or bystanders that some measured parameter or combination of measured parameters has exceeded the limits provided in the instruction set.

A signal which is within the test limits of normal signal 55 plus delta 58 is either sent to memory 44 or ignored, per the instruction set. A signal which exceeds the normal 55 plus delta 58, is sent to memory 44 to be recorded, and to logical gates 52 for further instructions. For example, assuming the managing physician instruction set includes a conditional, ".IF. (sensor 35 signal) .IS GREATER THAN. (normal 35) plus (delta 58 of sensor 35) .AND. (sensor 36 signal) .IS GREATER THAN. (normal 35) plus (delta 58 of sensor 36) .THEN. send signal to alarm device 23". This way a combination of several sensor outputs, each not exceeding upper or lower limit setup, but which, in combination, do exceed normal value plus delta, may be combined in to significant result.

Figure 3B:
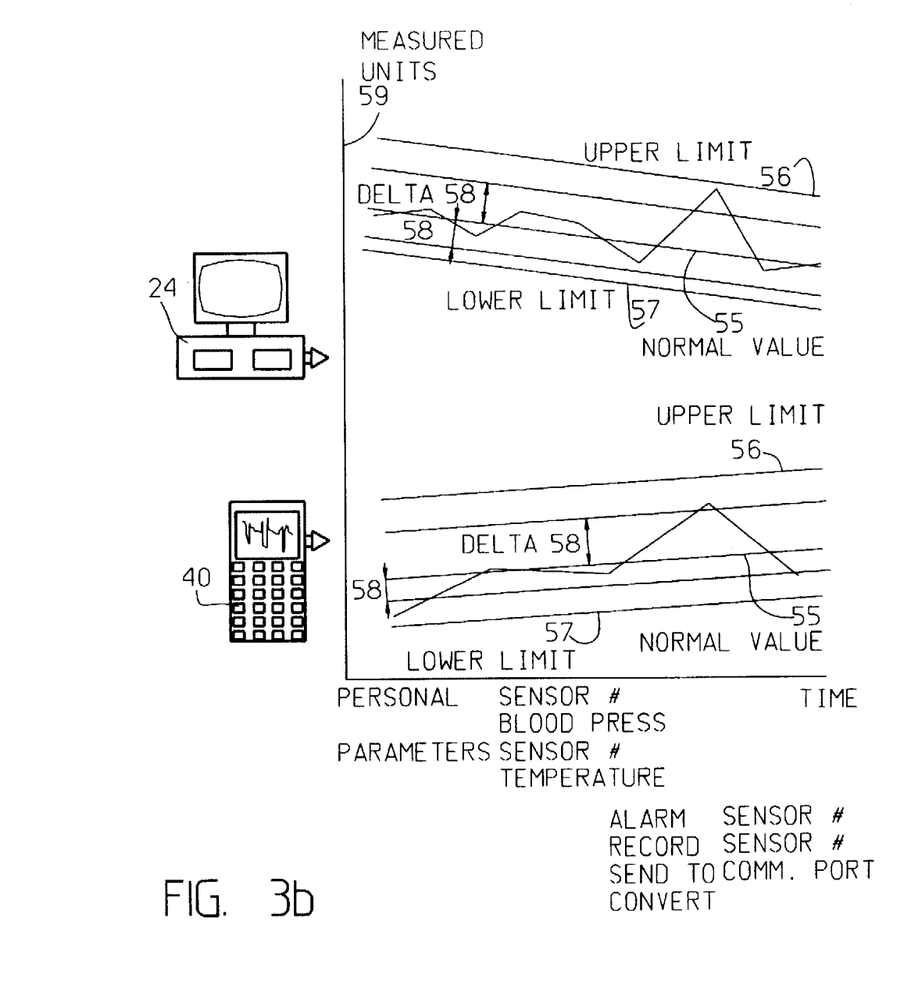
FIG. 3B shows schematically the available information from device 10.

In FIG. 3B, there are several graphs indicating the representation of instructions, data, and results, of device 10. The graphs in FIG. 3B may be interpreted in several ways: As a non-limiting example, one of the graphs may represent an actual sensor readout, its normal value, 55, delta, 58, upper limit, 56, and lower limit, 57; and the second graph shows the same.

By combining both readouts another conclusion may be derived, a primary benefit of non-determined systems, as neuron systems, fuzzy-logic, Neu-fuzz, and chaotic systems.

Another non-limiting example may be that one of the graphs represent actual sensor readout, and the other is anticipated body behaviour to a medication prescribed.

As a non-limiting example, both graphs may represent the anticipated behaviour. In case of a pregnant woman, when loading herself with glucose or sugar, at what time the fetus will change its heart beat on one of the graphs, and intensity of movements on the other one, while still maintaining limits 56 and 57, normal value 55 and delta 58.

Another possibility will be to show the anticipated behaviour while constantly monitoring actual sensor readout.

Of course, single or plurality of graphs may be represented.

Data accumulated in device 10 can be used to build a database of measured parameters of a monitored body. The managing physician may wish to use a medical diagnostic program such MEDICAL DOCTOR which is available from PIXEL PERFECT CORPORATION, Florida, and integrate measured parameters into a diagnostic module which can be installed in inquiring system 24 or 40. This module can request qualitative information such as the size of eye pupils, which, in combination with low blood pressure, may indicate brain damage. Another example would be the presence of a rash in combination with treatment by certain medications, which may be an indication of need to see a physician. Information such as this, on contra-indications of medications in combination with physical symptoms is published, for example in "Guide to Prescriptions and Over the Counter Drugs", copyright '88 by Dorling Kindersley Limited, London, ISBN 965-448-001-8. Such information may be integrated by the physician into a diagnostic module which can be installed in inquiring system 24 or 40.

Device 10 may be employed in one of several ways. For monitoring general vital signs of an individual, the device 10 is mounted on the body, and starts to monitor and collect data. When data collection is accomplished, the individual is required to approach a stationary data retrieving system, 24, such as a computer, or portable data retrieving system, 40, in which patient managing software is collecting transmitted data via communication means 13 and connecting cable 25, and prepare for presentation for a managing physician or for personnel view.

After data are retrieved, previously stored data may be erased and a new log is started.

In cases where rapid changes are expected, device 10 can be used for on-line monitoring, for which the device 10 is performing required monitoring, and continuously transmitting data to a data retrieving system, 24 or 40, via communication means, 13, and cable, 25.

In case a specific focusing on data collection or measurement is needed, a managing physician can express his point of interest via the communication means 13, so device 10 will perform tasks indicated. Furthermore, alarm set-points can be defined, such that when one or more pre-defined set-points or combination of set-points are exceeded an alarm will be given by an alarm device 23.

Moreover, a set-point can be defined by combining data coming from various sensors, even when data coming from any individual sensor is below the preset set-point for that specific individual sensor. This procedure makes it possible to use a combination of sensors to create an alarm which would not have been produced were each sensor monitored alone independently of the others.

The qualified personnel can read from device 10 by a stationary data retrieving system, 24, or portable data retrieving system, 40, current status, insert or call identification parameters, show histograms, inquire on possible reasons and suggested remedy, and read changes of monitored body as a result of actions taken.

Figure 4:
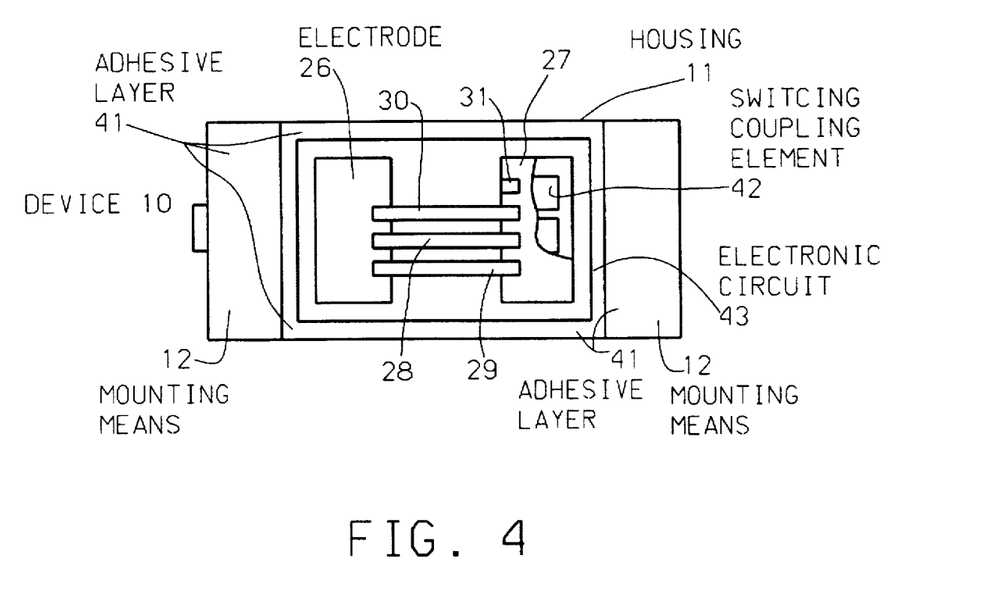
FIG. 4 shows schematically the side of the device which is in contact with the monitored body.

Referring to FIG. 4, there is shown the side of the device 10 which is in contact with the monitored body. The device is seen to feature at least two separate electrodes. One electrode is thick, 26, while one is substantially thin, 27. The electrodes are in contact with the monitored body and form a substantial base for mounting single or plurality of sensors. Also shown are mounting means 12 and a position on which an adhesive layer 41 can be implemented in order to allow device 10 to be mounted on a measured body surface.

For ease of presentation, four sensors are represented, 28, 29, 30 and 31. It is to be understood that more or fewer sensors may be used. As a non-limiting example, sensor 28 can measure heart electro-potential for which potential and ground electrodes are needed, sensor 29 can measure surface conductivity for which different polarity electrodes are needed, sensor 30 can measure local vascular pressures and uses electrode 27 as a membrane or a capacitor plate, while sensor 31 can measure temperature and uses electrode 26 as a heat sink.

Such an arrangement is not easily achieved, as different sensors may interfere with other sensors output. By way of a non-limiting example, a sensor which measures surface conductivity, 29, forms an electrical short circuiting which will interfere with a sensor measuring electrical potential, 28. A switching-coupling-element, 42, is mounted on the electronic circuit, 43, thus providing means to alternately connect and disconnect sensors which may interfere with each other.

The sensors provide their output in any convenient values, such as voltage, current, frequency, capacitance, inductance, resistance, TTL, and the like. As a non-limiting example, a thermocouple can indicate changes in external temperature through a change in voltage. Similarly for a piezoelectric crystal used to measure local pressure. By letting the managing physician define the type of sensor connected to device, 10, a measurement of voltage is achieved, however, differently interpreted to different sensor/logics. Furthermore, since the magnitude of these signals may vary by an order of magnitude or more, out-of-ranging may be implemented to shift the results to manageable value ranges.

Figure 5:
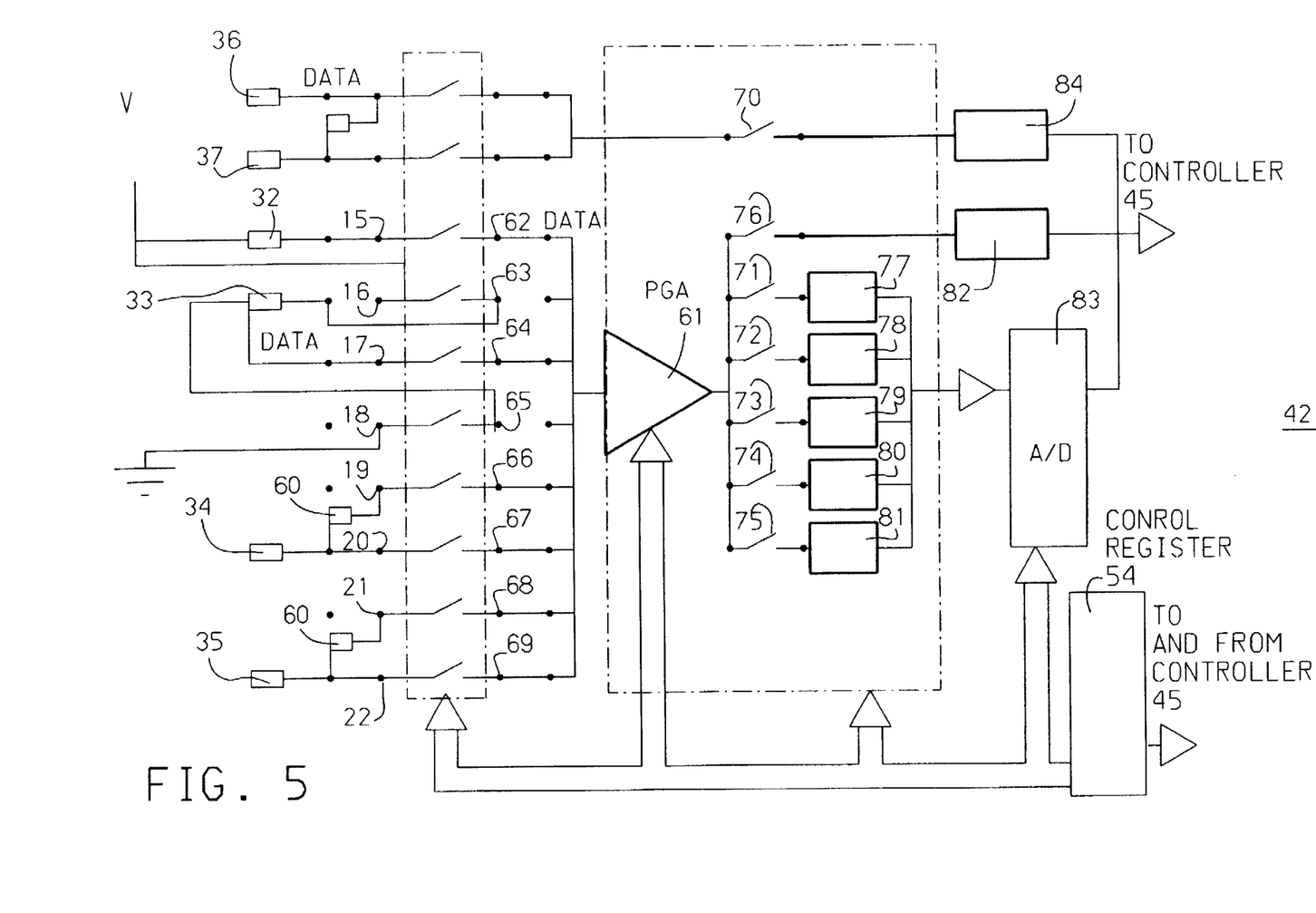
FIG. 5 shows schematically a block diagram of switching coupling measuring element.

FIG. 5 shows switching-coupling-measuring element, 42. Assuming sensor 32 is a simple sensor, the switching can be done by FET 62 on the data line through port 15, when the sensor is energized. Assuming sensor 33, when activated, can influence measurements being simultaneously performed by other sensors, such an influence may be minimized by using three FET'S, 63, 64, and 65, to switch power supply, ground, and data lines. Multiple FET switches may be used in parallel to reduce resistance in series with supply and ground lines. Of course, switching can be done simultaneously on all lines or only one of the lines at a time. In this arrangement, port 16 is dedicated to supply power to sensor 33, port 18 is dedicated to connect ground, and port 17 is dedicated to transfer data. Sensor 34 is connected to the data line through port 20 to be switched by FET 67 in the same manner as sensor 32. However, sensor 34 can be connected in parallel to impedance 60 connected to port 19. In this manner sensor 34 can transmit raw data via port 20 and FET 67, or via impedance 60 through port 19 and FET 66. An impedance can be defined as a component such as a resistor, or may be an RLC circuit or an integrated circuit.

Sensor 35 is connected in the same manner as sensor 34. When an average of sensors is required, sensors 34 and 35 can be connected simultaneously via ports 20 and 22, by FET's 67 and 69, or via impedance 60 via ports 19 and 21, and FET's 66 and 68. FET's 62–69 can be realized using NATIONAL AH0019, or 5011, or CD4066, which allows both digital and analogue data transfer. Data is transferred via a programmable gain amplifier, PGA 61, to the relevant measuring circuitry.

Voltage measuring circuitry, 77, current measuring circuitry, 78, capacitance measuring circuitry, 79, inductance measuring circuitry, 80, and resistance measuring circuitry, 81, are coupled by FET's, 71–75, respectively. The measurement circuits can be realized using techniques disclosed in prior art, such as the Wheatstone bridge, measuring over a shunt, or using methods found in any good-quality multimeters, such as manufactured by Fluke. The output of the measuring circuits, 77–81, is directed to A/D converter, 83, which transforms data into digital data manageable by controller, 45.

Frequency measurement is directed to counter, 82, via FET, 76, and sent to controller, 45. FET, 70, switches data from sensor 36 or 37 to controller, 45, via data buffer, 84. FET's 62–76 and PGA 61 are controlled by control register, 54, which can connect and disconnect any of FET's 62–69 alternatively or simultaneously, and one FET from group 71–76 in the same time, thus co-ordinating sensors with required gain and measuring circuit, and informing controller 45 of type of dam and origins. FET 70 can work with any of the FET's from group 71–76.

The arrangement mentioned in FIG. 5 can be realized by using as FET's 62–76, NATIONAL AH0019, AH5011, or CD 4066, which is suitable for analogue and digital data switching. The equivalent of a PGA 61 may also be implemented using FET switches for the gain-switching. An A/D converter, 83, such as industry-type ADC1210 is suitable for the above-mentioned applications. The A/D circuitry may also be realized by measuring the frequency output of a Voltage-to-frequency (V/F) converter, such as an LM131, which may be used to convert analog signals to frequency. Of course element 42 may be integrated into a single-component IC, and also integrated with controller 45 using ASIC technology.

When the instruction set is finished the sensors are wired to provide port connections corresponding to the port assignments in the instruction set, for example, as in FIG. 5.

This arrangement allows the minimization of the overall dimensions of device 10, and substantially reduces its cost.

Figures 6, 7:
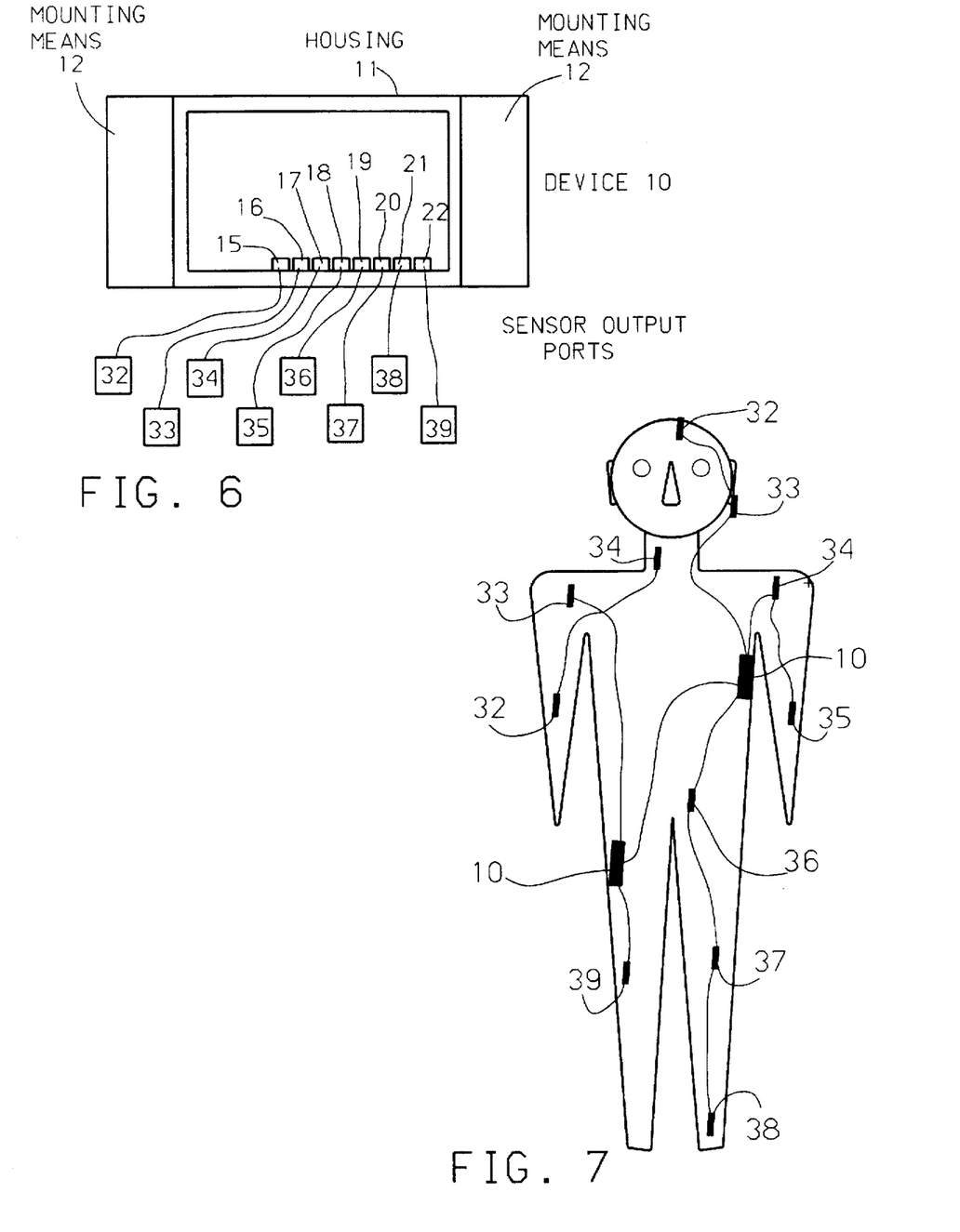
FIG. 6 shows schematically a connection of external sensors to the device.
FIG. 7 shows schematically a typical mounting of device and external sensors on a monitored body.

Referring to FIG. 6, it is shown that external sensors 32 to 39 can also be connected to device 10 via sensor output ports, 15 to 22, and work in conjunction with sensors 28, 29, 30 and 31.

FIG. 7 shows a typical mounting over a monitored body showing device 10 mounted on a body with associated external sensors, 32 to 39. Sensors 28 to 31 are not shown.

While the invention has been described with respect to a limited number of embodiments, it will be appreciated that many variations, modifications and other applications of the invention may be made.

What is claimed is:

1. A system for monitoring vital signs of a live body, comprising:
   (a) an inquiring device;
   (b) a portable monitoring device, said device including:
      (i) an electrical circuit, said circuit including a controller, data storage capability, and input ports, said electrical circuit being designed to read inputs and to store data;

(ii) a plurality of sensors connected to said electrical circuit inputs, each of said sensors providing said sensor's corresponding sensor output;

(iii) an alarm mechanism, said alarm mechanism designed to activate when a predetermined set point stored in said data storage capability is exceeded, said set point being based on at least one of said sensor outputs;

(iv) communication means for transferring said data to said inquiring device, and for downloading of related data such as personal identification parameters, operating software, forced measurement software, and alarm set-points from said inquiring device; and, (v) an instruction set for operation of said portable monitoring device.

2. A system as in claim 1, wherein said transferring of said data to said inquiring device occurs on-line.

3. A system as in claim 1, further comprising a housing, wherein said housing includes a plurality of electrodes on which at least one of said sensors is mounted.

4. A system as in claim 1, wherein said electrical circuit further includes a sensor switching coupling element which alternately connects and disconnects sensors.

5. A system as in claim 4, in which said sensor switching coupling element alternately connects and disconnects sensors which may interfere with each other.

6. A system as in claim 1, wherein said transferring of said data to said inquiring device and downloading of related data from said inquiring device is effected using optical impulses.

7. A system as in claim 1, wherein said transferring of said data to said inquiring device and downloading of related data from said inquiring device is effected using electronic wireless transmission.

8. A system as in claim 1 wherein said monitoring device is attached to the body using an adhesive layer.

9. A system as in claim 1, further comprising a database stored in said inquiring device, said database including symptoms and diagnoses for diagnosing the live body, based on said inputs from said sensors.

10. A system as in claim 9, further comprising a display for displaying said diagnoses.

11. A system as in claim 1, further including a display for displaying said inputs from said sensors.

12. A system as in claim 1, wherein said alarm set point is defined by a combination of said sensor outputs, each of which individual said sensor outputs is insufficient to exceed said sensor output's corresponding alarm set point.

13. A device as in claim 1, further comprising (c) GPS position locating capability.

14. A method for monitoring vital signs of a live body, comprising (a) providing:

(1) an inquiring device; and, (2) a portable monitoring device, said device including:

(i) an electrical circuit, said circuit including a controller, data storage capability, and input ports, said electrical circuit being designed to read inputs and to store data;

(ii) a plurality of sensors connected to said electrical circuit inputs, each of said sensors providing said sensor's corresponding sensor output;

(iii) an alarm mechanism, said alarm mechanism designed to activate when a predetermined set point stored in said data storage capability is exceeded, said set point being based on at least one of said sensor outputs;

(iv) communication means for transferring said data to said inquiring device, and for downloading of related data such as personal identification parameters, operating software, forced measurement software, and alarm set-points from said inquiring device; and, (b) providing said operating software to said inquiring and portable monitoring devices;

(c) providing diagnostic software and said alarm set-points to said inquiring device;

(d) downloading said diagnostic software and said set-points to said portable monitoring device;

(e) connecting said portable monitoring device to said live body; and, (f) operating said portable monitoring device, thereby providing (1) monitoring of said measured parameters of said live body; and, (2) comparing of said measured parameters with said set-points, thereby providing warning alarm capability if said measured parameters exceed said set-points.

15. A method as in claim 14, further comprising providing a database stored in said inquiring device, said database including symptoms and diagnoses for diagnosing the live body, based on said inputs from said sensors.

16. A method as in claim 15, further comprising providing software using said data and said database to provide capability of displaying any of: said sensor outputs, said alarm set-points, said alarm indicator status, said personal identification parameters, histograms of accumulated data, current diagnosis of state of health of the live body, possible reasons for abnormal physical data, possible reasons for abnormal diagnosis based on physical data, suggested treatment in case of abnormal diagnosis, anticipated behaviour of the body due to said suggested treatment, and monitoring physical changes resulting from actual treatment.

17. A method as in 14, further comprising transmitting said measured data to said inquiring device for more detailed diagnosis.

18. A method as in claim 14, further comprising (g) (1) providing GPS patient position locating capability; and, (2) transmitting patient location to said inquiring system.

* * * * *